(12) United States Patent
Olson

(10) Patent No.: US 11,957,903 B2
(45) Date of Patent: Apr. 16, 2024

(54) ELECTROPORATION CATHETER INCLUDING A DISTAL HOOP

(71) Applicant: St. Jude Medical, Cardilogy Division, Inc., St. Paul, MN (US)

(72) Inventor: Greg Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1086 days.

(21) Appl. No.: 16/220,334

(22) Filed: Dec. 14, 2018

(65) Prior Publication Data

US 2019/0201688 A1 Jul. 4, 2019

Related U.S. Application Data

(60) Provisional application No. 62/612,814, filed on Jan. 2, 2018.

(51) Int. Cl.
| A61B 18/14 | (2006.01) |
| A61N 1/32 | (2006.01) |
| A61B 17/00 | (2006.01) |
| A61B 18/00 | (2006.01) |

(Continued)

(52) U.S. Cl.
CPC .......... *A61N 1/327* (2013.01); *A61B 18/1492* (2013.01); *A61B 2017/00867* (2013.01); *A61B 2018/0016* (2013.01); *A61B 2018/00351* (2013.01); *A61B 2018/00511* (2013.01); *A61B 2018/00577* (2013.01); *A61B 2018/00613* (2013.01); *A61B 2018/1407* (2013.01);
(Continued)

(58) Field of Classification Search
CPC ...... A61B 18/1492; A61B 2017/00867; A61B 2018/0016; A61B 2018/00351; A61B 2018/00511; A61B 2018/00577; A61B 2018/00613; A61B 2018/1407; A61B 2018/1435; A61B 2034/301
See application file for complete search history.

(56) References Cited

U.S. PATENT DOCUMENTS

| 4,026,303 A * | 5/1977 | Babotai .................. A61N 1/057 607/127 |
| 5,482,037 A * | 1/1996 | Borghi .................. A61B 5/6856 606/124 |
| 7,263,397 B2 | 8/2007 | Hauck et al. |

(Continued)

OTHER PUBLICATIONS

International Search Report and Written Opinion for International Patent Application No. PCT/US2018/065646, dated Mar. 28, 2019, 18 pages.

*Primary Examiner* — Michael F Peffley
*Assistant Examiner* — Amanda L Zink
(74) *Attorney, Agent, or Firm* — Armstrong Teasdale LLP

(57) ABSTRACT

The present disclosure provides electroporation catheters that are capable of forming a loop, generally a circular loop, an oval loop, or like in shape, located on the distal end portion of a catheter shaft within the vasculature of an individual. The electroporation catheters of the present disclosure may be delivered into the vasculature of the individual in a straight conformation and allow for the formation of the loop once positioned in the desired location. Some embodiments of the present disclosure include an electroporation catheter that includes a loop member pull wire in a spiral or helical configuration on an inside surface of the distal end portion of the catheter shaft.

10 Claims, 6 Drawing Sheets

(51) Int. Cl.
*A61B 34/30* (2016.01)
*A61M 25/01* (2006.01)
(52) U.S. Cl.
CPC . *A61B 2018/1435* (2013.01); *A61B 2034/301* (2016.02); *A61M 25/0133* (2013.01)

(56) References Cited

U.S. PATENT DOCUMENTS

| | | | |
|---|---|---|---|
| 10,391,274 B2* | 8/2019 | Giles | A61M 25/09041 |
| 2005/0010095 A1* | 1/2005 | Stewart | A61B 18/1492 |
| | | | 606/41 |
| 2008/0234661 A1 | 9/2008 | Hastings et al. | |
| 2012/0197246 A1* | 8/2012 | Mauch | A61B 18/1492 |
| | | | 606/41 |
| 2015/0126996 A1 | 5/2015 | Tegg et al. | |
| 2016/0128767 A1* | 5/2016 | Azamian | A61B 18/1492 |
| | | | 606/41 |
| 2019/0125437 A1* | 5/2019 | Govari | A61B 5/6852 |
| 2021/0330310 A1* | 10/2021 | Giles | A61B 1/0055 |
| 2022/0023593 A1* | 1/2022 | Giles | A61B 1/00148 |

\* cited by examiner

ELECTROPORATION CATHETER INCLUDING A DISTAL HOOP

CROSS REFERENCE TO RELATED APPLICATIONS

This application claims priority to provisional application Ser. No. 62/612,814, filed Jan. 2, 2018, which is incorporated herein in its entirety.

A. FIELD OF THE DISCLOSURE

The present disclosure relates generally to medical devices that are used in the human body. In particular, in many embodiments, the present disclosure relates to unidirectional and bidirectional electroporation catheters capable of forming a loop at the distal portion of the catheter shaft inside the vasculature of an individual to improve overall performance and maneuverability of the catheter shaft and loop during a procedure.

B. BACKGROUND

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

Typically, a catheter is deployed and manipulated through a patient's vasculature to the intended site, for example, a site within a patient's heart. The catheter typically carries one or more electrodes that can be used for cardiac mapping or diagnosis, ablation, and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. These lesions disrupt undesirable cardiac activation pathways and thereby limit or prevent errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to selectively position the distal portion of the catheter during an electrophysiological procedure. The proximal end of the catheter can be manipulated to guide the catheter through a patient's vasculature. The distal tip can be deflected by a pull wire attached at the distal end of the catheter and extending proximally to an actuator in a control handle that controls the application of tension on the pull wire. In many cases, the distal tip of the catheter may include a loop member (or spiral loop member) to further diagnostic and treatment application.

BRIEF SUMMARY OF THE DISCLOSURE

The present disclosure generally relates to electroporation catheters and electroporation catheter handles that are capable of forming a loop, generally a circular loop, an oval loop, or like in shape, located on the distal tip of a catheter shaft within the vasculature of an individual. The electroporation catheters of the present disclosure may be delivered into the vasculature of the individual in a straight conformation and allow for the formation of the loop on a distal end portion thereof once positioned in the desired location. Some embodiments of the present disclosure include an electroporation catheter that includes a loop member pull wire arranged in a spiral or helical configuration on an inside surface of at least the distal end portion of the catheter shaft. Other embodiments of the present disclosure include the use of a memory shape wire that is formed into a preset conformation including a loop member such that once inserted into the body of an individual, the preset loop member conformation may take shape. Still other embodiments of the present disclosure include the use of a temperature-sensitive memory shape wire that allows for the formation of a loop member conformation on a distal end at a certain temperature within the body of an individual.

In one embodiment, the present disclosure is directed to an electroporation catheter comprising: (i) a longitudinally-extending catheter shaft comprising a proximal end portion and a distal end portion; (ii) a handle attached to the proximal end portion of the catheter shaft; and (iii) a loop member pull wire in a spiral configuration on an inside surface of the distal end portion of the catheter shaft for forming a loop member on the distal end portion of the catheter shaft, wherein the loop member pull wire is attached to an attachment point on the distal end portion of the catheter shaft and to an attachment point on the handle.

In another embodiment, the present disclosure is directed to a method of introducing an electroporation catheter into a pulmonary vein of an individual. The method comprises: (i) forming a memory shape wire into a desired preset conformation including a loop member; (ii) introducing the memory shape wire into a delivery shaft, the memory shape wire having a conformation in the delivery shaft different from the preset conformation; (iii) introducing and positioning the delivery shaft including the memory shape wire into the pulmonary vein of the individual; (iv) removing the delivery shaft from the memory shape wire to allow the memory shape wire to achieve its preset conformation including the loop member in the pulmonary vein; and (v) introducing an electroporation catheter including one or more electrodes over the memory shape wire in the pulmonary vein.

In another embodiment, the present disclosure is directed to a method of introducing an electroporation catheter into a pulmonary vein of an individual. The method comprises: (i) forming a memory shape braided tube into a preset conformation including a loop member, wherein the preset conformation is achieved at a temperature of about 35° C. or higher, and wherein the memory shape braided tube includes a guidewire lumen; (ii) introducing the memory shape braided tube into an outer shaft, the memory shape braided tube having a conformation in the outer shaft different from the preset conformation, wherein the outer shaft includes one or more electrodes; (iii) introducing and positioning the outer shaft including the memory shape braided tube into the pulmonary vein of the individual over a guidewire; and (iv) removing the guidewire and allowing the memory shape braided tube to achieve its present conformation such that the memory shape braided tube and the outer shaft including one or more electrodes achieve a conformation including a loop member.

In another embodiment, the present disclosure is directed to an electroporation catheter comprising: (i) a longitudinally-extending outer catheter shaft comprising a proximal end portion and a distal end portion; (ii) a handle attached to the proximal end portion of the catheter shaft; and (iii) a memory shape alloy inner shaft disposed in the outer catheter shaft, the memory shape alloy inner shaft including a guidewire lumen therein, wherein the memory shape alloy inner shaft assumes a first conformation at a first temperature and a second conformation at a second temperature greater than the first temperature, and wherein the second conformation includes a loop member on a distal end of the memory shape alloy inner shaft.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
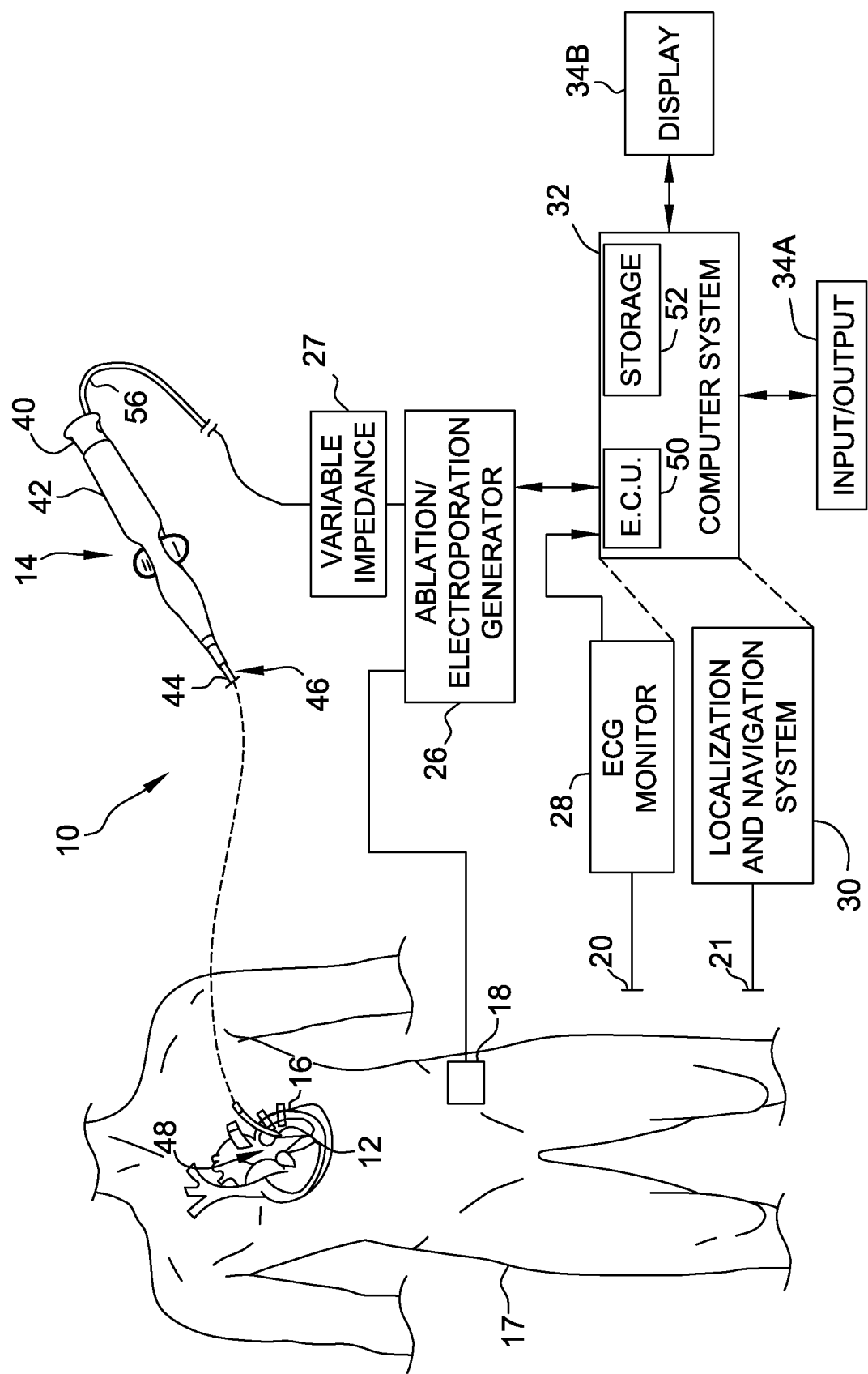
FIG. 1 is a schematic and block diagram view of a conventional medical system incorporating various embodiments of the present disclosure.

The present disclosure provides medical devices including electroporation catheter systems, electroporation catheters, and electroporation catheter handles suitable for use in the human vasculature for known medical procedures, as well as methods of utilizing the electroporation catheter systems, catheters, and catheter handles. Electroporation catheter systems, catheters, and catheter handles of the multiple embodiments of the present disclosure include a loop member, such as a circular loop member or other shaped loop member, on a distal end portion of a catheter shaft that may be formed once inside the body of an individual; that is, the catheter shaft may be introduced into the vasculature of the individual in a straight conformation to facilitate steering and once a desired location is reached inside of the individual (the pulmonary vein, for example) the loop member may be formed thus resulting in improved circular contact of the electrodes and the surrounding tissue. The disclosed embodiments may lead to more consistent and improved patient outcomes. For purposes of this description, the present disclosure will be generally described in connection with numerous embodiments of a bidirectional catheter including a circular loop member on a distal end portion thereof. It is contemplated, however, that the described features and methods of the present disclosure as described herein may be incorporated into any number of bidirectional or other catheters or other medical devices having a loop member of another shape (oval, etc.) as would be appreciated by one of ordinary skill in the art based on the disclosure herein.

In many embodiments of the present disclosure, the shaft of the electroporation catheter will include a loop member pull wire set in a spiral or helical configuration on an inside surface of at least the distal end portion of the catheter shaft. This loop member pull wire may be attached to an attachment point on the distal end of the catheter shaft and to an attachment point on the catheter handle, such that the catheter shaft may be introduced into the vasculature of an individual in a straight conformation. Once the distal end portion of the catheter shaft has been properly positioned within the vasculature, the loop member pull wire may be activated resulting in the formation of a loop member on the distal end portion of the catheter due to the spiral or helical conformation of the pull wire and the forces generated thereby upon activation. Additionally, in many embodiments, this setup allows the loop member to be straightened again prior to removal from the vasculature of the individual. As described more fully herein, various portions of the catheter shaft may be formed from materials having varying degrees of hardness to further the formation of the desired loop member. Other embodiments described herein may include the use of memory shape alloy wires having a preset loop conformation and temperature sensitive wires also having a preset loop conformation, as well as multiple methods of use of these catheters.

Referring now to the drawings, FIG. 1 is a diagrammatic and block diagram view of a system 10 for diagnostic purposes, anatomical mapping, electroporation therapy, and/or ablation therapy. In general, the various embodiments include an electrode assembly disposed at the distal end of a catheter shaft. As used herein, "proximal" refers to a direction toward the end of the catheter near the clinician and "distal" refers to a direction away from the clinician and (generally) inside the body of an individual.

System 10 includes a catheter electrode assembly 12 including at least one catheter electrode configured to be used as described below. Electrode assembly 12 is incorporated as part of a medical device such as a catheter 14 for electroporation therapy, diagnostic, mapping, and/or therapeutic procedures. For example, electrode assembly 12 may be used for electroporation therapy of tissue 16 in a body 17 of an individual. In the illustrative embodiment, tissue 16 comprises heart or cardiac tissue. It should be understood, however, that embodiments may be used to conduct electroporation therapy with respect to a variety of other body tissues.

FIG. 1 further shows a plurality of return electrodes designated 18, 20, and 21, which are diagrammatic of the body connections that may be used by the various subsystems included in the overall system 10, such as an ablation generator 26, an electrophysiology (EP) monitor such as an ECG monitor 28, a localization and navigation system 30 for visualization, mapping and navigation of internal body structures. In the illustrated embodiment, return electrodes 18, 20, and 21 are patch electrodes. It should be understood that the illustration of a single patch electrode is diagrammatic only (for clarity) and that such sub-systems to which these patch electrodes are connected may, and typically will, include more than one patch (body surface) electrode. In other embodiments, return electrodes 18, 20, and 21 may be any other type of electrode suitable for use as a return electrode including, for example, one or more catheter electrodes. Return electrodes that are catheter electrode may be part of electrode assembly 12 or part of a separate catheter (not shown). System 10 may further include a main computer system 32 (including an electronic control unit 50 and data storage—memory 52), which may be integrated with system 30 in certain embodiments. System 32 may further include conventional interface components, such as various user input/output mechanisms 34*a* and a display 34*b*, among other components.

Ablation generator 26 includes radiofrequency (RF) ablation and electroporation generators (not separately shown) to allow system 10 to be used for RF ablation and electroporation procedures. Ablation generator 26 is sometimes referred to herein as ablation/electroporation generator 26. In other embodiments ablation generator may include other ablation generators to allow system to perform any other ablation procedure (such as cryoablation). Ablation generator 26 is configured to energize the electrode element(s) in accordance with an ablation or electroporation energization strategy, which may be predetermined or may be user-selectable. Although illustrated as a single component, generator 26 may include separate ablation and electroporation generators. For electroporation-induced primary necrosis therapy, generator 26 may be configured to produce an electric current that is delivered via electrode assembly 12 as a pulsed electric field in the form of short-duration DC pulses (e.g., a nanosecond to several milliseconds duration, 0.1 to 20 ms duration, or any duration suitable for electroporation) between closely spaced electrodes capable of delivering an electric field strength (i.e., at the tissue site) of about 0.1 to 1.0 kV/cm. The amplitude and pulse duration needed for irreversible electroporation are inversely related. As pulse durations are decreased, the amplitude must be increased to achieve electroporation.

The electroporation portion of generator 26, sometimes also referred to herein as a DC energy source, is a monophasic electroporation generator 26 configured to generate a series DC energy pulses that all produce current in the same direction. In other embodiments, electroporation generator is biphasic or polyphasic electroporation generator configured to produce DC energy pulses that do not all produce current in the same direction. In some embodiments, electroporation generator 26 is a monophasic defibrillator. The defibrillator is configured to output energy in DC pulses at selectable energy levels, such as fifty joules, one hundred joules, two hundred joules, and the like. Other embodiments may have more or fewer energy settings and the values of the available setting may be the same or different. For successful electroporation, some embodiments utilize the two hundred joule output level. Electroporation generator 26 may output a DC pulse having a peak magnitude of about between about negative one kilovolt (kV) and about negative two kV at the two hundred joule output level. In some embodiments, electroporation generator 26 outputs a DC pulse having a peak magnitude of about between about negative 1.5 kV and about negative 2.0 kV. Other embodiments may output any other suitable voltage, including a positive voltage. In some embodiments, the monophasic defibrillator is a Lifepak 9 defibrillator available from Physio-Control, Inc., of Redmond, Washington, USA.

When used for ablation procedures, generator 26 outputs radio frequency (RF) energy to catheter 14 through cable 56. The RF energy leaves catheter 14 through electrodes of electrode assembly 12. The RF energy travels through the patient's body to return electrode 118. The dissipation of the RF energy in the body increases the temperature near the electrodes, thereby permitting ablation to occur. In the exemplary embodiment set forth herein, system 10 is suitable for use in performing renal denervation. It is understood, however, that the system may be used for other treatments without departing from the scope of this disclosure.

A selection interface 29 allows catheter 14 to be selectively connected to electroporation generator 26 (through variable impedance 27) or to localization and navigation system 30 (through computer system 32). Moreover, selection interface 29 is operable to selectively couple different electrodes to electroporation generator or localization and navigation system 30. In the example embodiment, selection interface selectively couple a specific portion (less than all) of the electrodes to the localization and navigation system 30 during mapping, navigation, etc., and couples all of the electrodes to the electroporation generator 26 during electroporation. Other embodiments may selectively couple all electrodes or different groups of electrodes to electroporation generator or localization and navigation system 30.

A variable impedance 27 allows the impedance of the system to be varied to limit arcing from the catheter electrode of catheter 14, particularly during electroporation procedures. Moreover, variable impedance 27 may be used to change one or more characteristics, such as amplitude, duration, pulse shape, and the like, of an output of electroporation generator 26. Although illustrated as a separate component, variable impedance 27 may be incorporated in catheter 14 or generator 26. Variable impedance 27 includes one or more impedance elements, such as resistors, capacitors, or inductors (not shown) connected in series, parallel, or combinations of series and/or parallel. In the illustrated embodiment, variable impedance 27 is connected in series with catheter 14. Alternatively, the impedance elements of variable impedance 27 may be connected in parallel with catheter 14 or in a combination of series and parallel with catheter 14. Moreover, in other embodiments, the impedance elements of variable impedance 27 are connected in series and/or parallel with return electrode 18. Some embodiments include more than one variable impedance 27, each of which may include one or more impedance elements. In such embodiments, each variable impedance 27 may be connected to a different catheter electrode or group of catheter electrodes to allow the impedance through each catheter electrode or group of catheter electrodes to be separately varied. In other embodiments, the impedance of system 10 may not need to be varied and variable impedance 27 may be omitted. Moreover, in some embodiments, variable impedance 27 may be selectively or automatically bypassed when not needed, such as when performing ablation.

In the illustrative embodiment, the variable impedance is a variable resistance. In some embodiments variable impedance 27 includes one or more resistors (not shown) removably connected between generator 26 and catheter 14. The resistors may be connected in series, parallel, or any combination of series and parallel connections to produce a desired system impedance. Some or all of the resistors may be added, removed, or connected differently to vary the system impedance. In some other embodiments, variable impedance 27 is variable resistor, such as a rheostat or a potentiometer. In still other embodiments, variable impedance 27 includes resistors coupled together by one or more switches to allow the resistors to be selectively switched in and out of the connection between generator 26 and catheter 14. Such a variable impedance 27 may also be configured to allow some or all of the resistors to be selectively connected together in series or in parallel with each other. In some embodiments, variable impedance 27 is variable in response to an appropriate control signal from computer system 32. The resistors may be any suitable type of resistor. In all embodiments, the resistors (or other impedance elements) have relatively high energy ratings sufficient to handle the output of generator 26 without being damaged. In some embodiments, variable impedance 27 includes Ohmite PulsEater resistors available from Ohmite Mfg. Co. of Warrenville, IL, USA. With continued reference to FIG. 1, as noted above, catheter 14 may comprise functionality for electroporation and in certain embodiments also an ablation function (e.g., RF ablation). It should be understood, however, that in those embodiments, variations are possible as to the type of ablation energy provided (e.g., cryoablation, ultrasound, etc.).

In the illustrative embodiment, catheter 14 includes a cable connector or interface 40, a handle 42, and a shaft 44 having a proximal end 46 and a distal end 48. Catheter 14 may also include other conventional components not illustrated herein such as a temperature sensor, additional electrodes, and corresponding conductors or leads. The connector 40 provides mechanical and electrical connection(s) for cable 56 extending from generator 26. The connector 40 may comprise conventional components known in the art and as shown is disposed at the proximal end of catheter 14.

Handle 42 provides a location for the clinician to hold catheter 14 and may further provide means for steering or the guiding shaft 44 within body 17. For example, handle 42 may include means to change the length of one or more guidewires extending through catheter 14 to distal end 48 of shaft 44 or other means to steer shaft 44. Moreover, in some embodiments, handle 42 may be configured to vary the shape, size, and/or orientation of a portion of the catheter. Handle 42 is also conventional in the art and it will be understood that the construction of handle 42 may vary. In an alternate exemplary embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14. Shaft 44 is an elongated, tubular, flexible member configured for movement within body 17. Shaft 44 is configured to support electrode assembly 12 as well as contain associated conductors, and possibly additional electronics used for signal processing or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be advanced, retracted and/or steered or guided through body 17 to a desired location such as the site of tissue 16, including through the use of guidewires or other means known in the art.

In embodiments of the present disclosure, catheter 14 is a hoop catheter (also sometimes referred to herein as a loop catheter) having catheter electrodes (not shown in FIG. 1) distributed about one or more hoops at the distal end of shaft 44. The diameter of the hoop(s) (sometimes referred to herein as "loops") may be variable in some embodiments. In some embodiments, the hoop catheter diameter is variable by about ten millimeters (mm) between a minimum diameter and a maximum diameter. The minimum diameter in some embodiments may be selected between about thirteen mm and about twenty mm when the catheter 14 is manufactured. With a ten mm range of variability, such catheters would have a maximum diameter between twenty-three mm and thirty mm. In other embodiments, the hoop diameter is variable between about fifteen mm and about twenty eight mm, between about thirteen mm and about twenty-three mm, or between about seventeen mm and about twenty-seven mm. Alternatively, in many embodiments of the present disclosure, the electroporation catheter may be a fixed diameter hoop catheter or may be variable between different diameters.

In the exemplary embodiment, all catheter electrodes are substantially the same. In some embodiments, catheter 14 has fourteen catheter electrodes. In other embodiments, catheter 14 includes ten catheter electrodes, twenty catheter electrodes, or any other suitable number of electrodes for performing one or more desired procedure. In some embodiments, the catheter electrodes are ring electrodes, such as platinum ring electrodes. Alternatively, the catheter electrodes may be any other suitable type of electrodes, such as single sided electrode or electrodes printed on a flex material. In various embodiments, the catheter electrodes have lengths of 1.0 mm, 2.0 mm, 2.5 mm, and/or any other suitable length.

In other embodiments, catheter 14 includes two or more different types of electrodes. The types of electrodes may differ in size, material, and/or any other suitable characteristic. In some embodiments, catheter 14 has eight first type catheter electrodes and fourteen second type catheter electrodes grouped as seven pairs of second type catheter electrodes. In other embodiments, catheter 14 includes any other suitable number of first and second type catheter electrodes for performing electroporation. Moreover, in other embodiments, the ratio of first type catheter electrodes to second type catheter electrodes is other than 8:14. Ratios of first type catheter electrodes to second type catheter electrodes other than 8:14 may require increasing the size of the shaft of the catheter. In some embodiments, the catheter electrodes are ring electrodes, such as platinum ring electrodes. Alternatively, the catheter electrodes may be any other suitable type of electrodes, such as single sided electrode or electrodes printed on a flex material. In some embodiments, the first type catheter electrodes have lengths of 2.5 mm, and the second type catheter electrodes have lengths of about 1.3 mm. In other embodiments, the first type catheter electrodes have lengths between 2.5 mm and 3.1 mm, between 2.2 mm and 3.1 mm, or any other suitable length for use as described herein. In various embodiments, the second type catheter electrodes have lengths between 1.0 mm and 1.3 mm, between 0.9 mm and 1.5 mm, or any other suitable length for use as described herein.

The localization and navigation system 30 may be provided for visualization, mapping and navigation of internal body structures. System 30 may comprise conventional apparatus known generally in the art (e.g., an EnSite NAVX™ Navigation and Visualization System, commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference). In various embodiments, localization and navigation system 30 uses the second type catheter electrodes as bipolar pairs for visualization, mapping and navigation of internal body structures, as described in more detail below. It should be understood, however, that this system is exemplary only and not limiting in nature. Other technologies for locating/ navigating a catheter in space (and for visualization) are known, including for example, the CARTO navigation and location system of Biosense Webster, Inc., the AURORA® system of Northern Digital Inc., commonly available fluoroscopy systems, or a magnetic location system such as the gMPS system from Mediguide Ltd. In this regard, some of the localization, navigation and/or visualization system would involve a sensor be provided for producing signals indicative of catheter location information, and may include, for example one or more electrodes in the case of an impedance-based localization system, or alternatively, one or more coils (i.e., wire windings) configured to detect one or more characteristics of a magnetic field, for example in the case of a magnetic-field based localization system.

In accordance with one embodiment of the present disclosure, there is provided an electroporation catheter for use in an electroporation system that may be introduced into the vasculature of an individual in a straight or substantially non-curved conformation. Once the electroporation catheter is properly positioned within the vasculature, a loop on a distal end portion is formed to allow for accurate placement of the loop and improved electrode contact between the loop (which includes one or more electrodes) and the tissue of an individual. The catheter may include one or more lumens for guidewires, fluids, etc. In this embodiment, all or at least a portion of the distal end portion of the catheter shaft includes at least one loop member pull wire in a spiral or helical configuration on an inside surface of the catheter shaft for forming a loop member on the distal end portion of the catheter shaft upon activation. In embodiments where more than one loop member pull wire is utilized, the loop member pull wires may be offset on the inside surface of the distal end portion of the catheter shaft, or may not be offset. For example, if two loop member pull wires are used, in one embodiment they may be offset from one another by 180 degrees around the inside surface of the distal end portion of the catheter shaft. Alternatively, the two loop member pull wires may not be offset at all and may be present substantially next to each other on the inside surface of the distal end portion of the catheter shaft. In many embodiments, the loop member pull wire, or loop member pull wires, will complete at least one revolution, or at least two revolutions, or at least three revolutions or more on the inside surface of the distal end portion of the catheter shaft.

This spiral or helical loop member pull wire present on the inside surface of at least a portion of the distal end portion is attached to an attachment point on the distal end portion of the catheter shaft and to an attachment point on the handle, and may be activated (to form the desired loop member) by one or more actuating mechanisms on the catheter handle. Upon activation, the loop member pull wire is urged toward the proximal end of the catheter thus resulting in the distal end portion of the catheter forming a loop member. The pitch or wind of the spiral or helical loop member pull wire around the inside surface of the distal end portion of the catheter shaft may be controlled, adjusted, and/or configured to control and adjust the diameter and exact size of the loop that is ultimately formed on the distal end portion of the catheter shaft.

Figure 2:
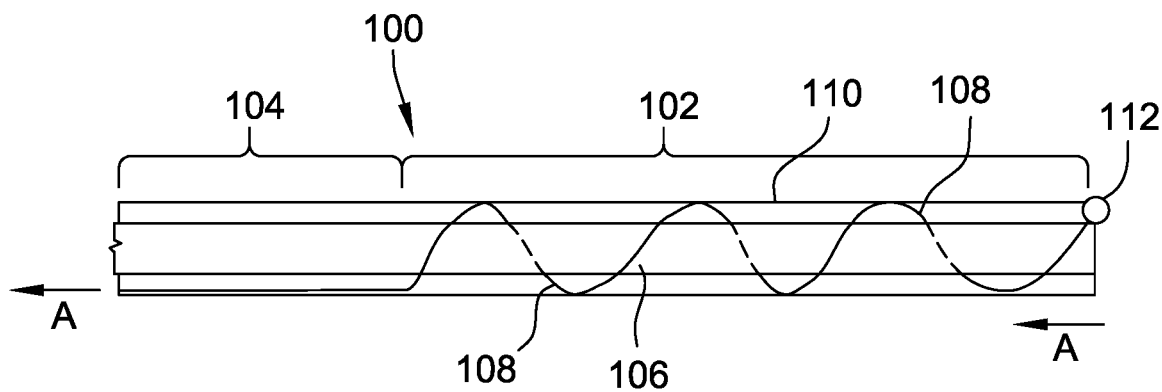
FIG. 2 is a cut-away illustration of a portion of a catheter shaft including a spiral loop member pull wire in accordance with one embodiment of the present disclosure.

Referring now to FIG. 2, there is shown a cut away view of a portion of a longitudinally-extending catheter shaft including a helical loop member pull wire in accordance with one embodiment of the present disclosure. Catheter shaft 100 includes distal end portion 102, proximal end portion 104, and lumen 106. As illustrated in FIG. 2, distal end portion 102 of catheter shaft 100 includes loop member pull wire 108 configured in a spiral configuration about inside surface 110 of distal end portion 102. Loop member pull wire 108 is attached on one end to attachment point 112 located in distal end portion 102 of catheter shaft 100 and is attached on a second end to an attachment point in a catheter handle (not shown in FIG. 2). When loop member pull wire 108 is urged in a direction along arrow A, distal end portion 102 of catheter shaft 100 forms a loop member due to the spiral configuration of loop pull wire 108 in distal end portion 102 of catheter shaft 100 as torque and twist is applied to loop pull wire 108 along with foreshortening. Catheter shaft 100 may include one or more electroporation electrodes (not shown in FIG. 2) on distal end portion 102 of catheter 100.

Figure 3A:
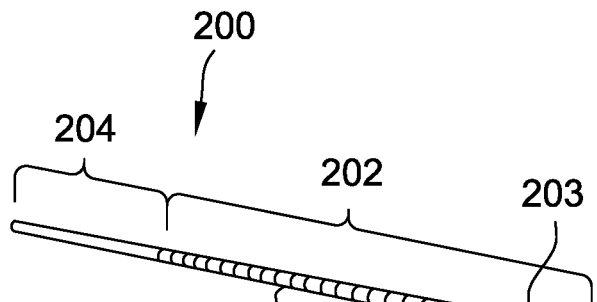
FIGS. 3A-3D illustrate the formation of a loop member on the distal end portion of a catheter shaft in accordance with the present disclosure.
Figure 3B:
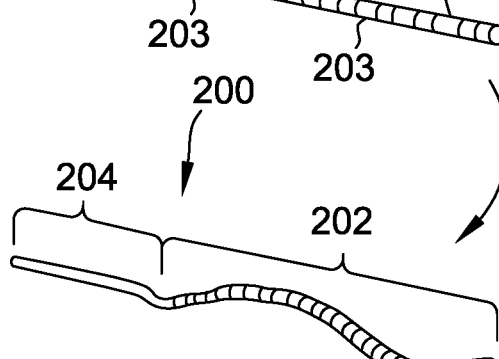
Figure 3C:
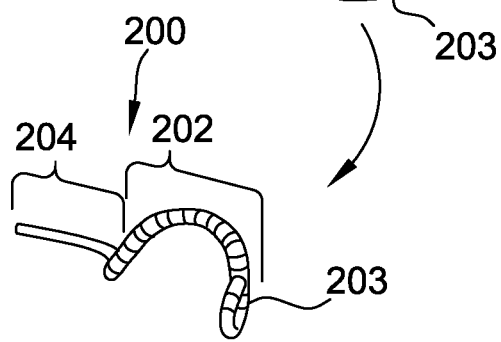
Figure 3D:
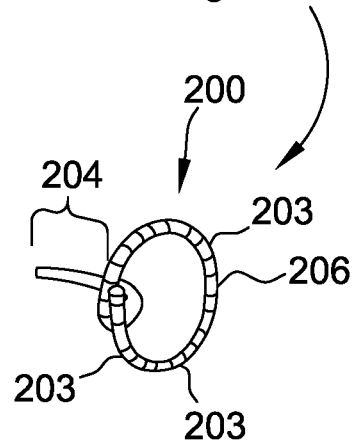

Referring now to FIGS. 3A-3D, there is illustrated the formation of a loop member on the distal end portion of a catheter shaft upon application of a force in the proximal direction (arrow A in FIG. 2) in accordance with the present disclosure. FIG. 3A illustrates catheter shaft 200 including distal end portion 202 and proximal end portion 204 in a straight conformation. Distal end portion 102 additionally includes electrodes 203. FIGS. 3B, 3C, and 3D illustrate catheter shaft 200 forming loop member 206 (comprised of distal end portion 202) through a change in conformation of distal end portion 202 as loop member pull wire (not shown in FIGS. 3A-3D) is urged in a proximal direction (See arrow A in FIG. 1).

As noted above, the catheter shaft may be constructed of conventional materials including, for example, a braided polyurethane or similar braided or unbraided material. The catheter shaft may, in many embodiments, include one or more layers of materials in addition to the braided polyurethane to impart additional benefits or characteristics to the catheter shaft. In some embodiments, these one or more layers may include layers formed of a polyether block amide material, such as a PEBAX® material. Additional PEBAX® layers may use one or more PEBAX® materials. In one desirable embodiment, the catheter shaft may include one or more layers of a polyether block amide material that transition from harder to softer along that catheter shaft from the proximal end portion to the distal end portion; that is, there may be a transition in hardness from the proximal end portion to the distal end portion of the catheter shaft such that the one or more layers of polyether block amide material present on the catheter shaft comprise softer materials on the distal end portion of the catheter shaft as compared to the proximal end portion of the catheter shaft. Such transitions of the hardness or stiffness of the polyether block amide material (or other suitable material or materials) may further facilitate the formation of the loop member described herein upon urging of the loop member pull wire. In one specific embodiment, a catheter shaft may have a hardness in the proximal end portion of from about 70 to about 72D and transition through the distal end portion through a hardness of from about 30 to about 40D; that is, the hardness of the catheter shaft will decrease from the proximal end portion to the distal end portion to facilitate the forming of the loop member. In some embodiments, the hardness transition may be a gradual transition over a desired length of the catheter shaft.

The loop member pull wire on at least the inside surface of the distal end portion of the catheter shaft as described herein may be formed from any conventional material including, for example, stainless steel and the like. In one specific embodiment of the present disclosure, the loop member pull wire is formed from a memory-shape alloy, such as a nickel-titanium metal alloy. Such memory-shape alloys tend to have a temperature induced phase change that will cause the material to have a preferred configuration that can be fixed by heating the material above a certain transition temperature to induce a change in the phase of the material. When the alloy is cooled back down, the alloy will "recall" the shape it was in during the heat treatment and will tend to assume that configuration unless constrained from doing so. One particularly desirable memory shape alloy for use in the present disclosure is nitinol, an approximately stoichiometric alloy of nickel and titanium, which may also include minor amounts of other metals to achieve desired properties. Nickel-titanium alloys are very elastic and are commonly referred to as "superelastic" or "pseudoelastic." The elasticity of these alloys helps a formed member return to an expanded configuration for deployment inside of the body following passage in a distorted or collapsed form through a delivery catheter. Nitinol is a particularly desirable alloy for forming the loop member pull wire.

Prior to introducing the nickel-titanium metal alloy (or other memory-shape alloy) into the inside surface of the distal end portion of the catheter shaft, the alloy may be subjected to a heat-treatment process as is known in the art to impart a memory shape conformation in the form of a helical or spiral conformation to the alloy; that is, the nickel-titanium metal alloy is heat set to a helical or spiral conformation. After this treatment, the metal alloy is stretched straight (i.e., constrained) and introduced as the loop member pull wire into the distal end portion of the catheter shaft. The heat set conformation is not sufficiently strong to allow the metal alloy to cause the distal end portion of the catheter shaft to form a loop member by itself; that is, once introduced into the inside surface of the distal end portion of the catheter shaft the preset metal allow remains elongated. Once a force in a proximal direction as described herein is provided, the preset metal alloy assists in the formation of the loop member pull wire due to the heat-treatment or other preset process; that is, because the metal alloy is shaped as descried above, it assists in the formation of the loop member to achieve its desired heat set conformation.

In many embodiments, the loop member pull wire as described herein may be positioned between two or more tubes of the catheter shaft, such as between an inner tube and an outer tube. In other embodiments, the loop member pull wire may be integral in the catheter shaft wall design. In many embodiments, the loop member pull wire will be brazed, welded, or otherwise affixed to a shaft ring or tip. In other embodiments, when the loop member pull wire is formed from a fibrous material, it may be affixed to a crimp ring or similar. In other embodiments, an adhesive may optionally be used to secure the loop member pull wire. In other embodiments, a second loop member pull wire may be utilized to assist in the straightening of the catheter shaft and/or assisting in furthering the formation of the loop member.

Figure 4:
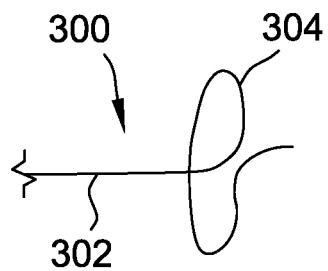
FIG. 4 illustrates a core wire having a heat set conformation including a loop member for use in embodiments of the present disclosure.

In another embodiment of the present invention, an electroporation catheter capable of forming a loop member on a distal end portion thereof may be introduced into the vasculature of an individual in two separate steps wherein a core wire is first introduced into the vasculature in a straight conformation and subsequently forms the desired loop member once positioned. In this embodiment, a core wire which may be formed from a memory shape alloy, such as a nickel-titanium alloy or the like as described herein, is first subjected to a conventional heat treatment or other suitable treatment to introduce a preset conformation on the core wire. The diameter of the core wire may depend on the outer diameter of the catheter and its related construction, but will typically not be larger than about 0.016 inches to about 0.020 inches, and in some embodiments may be about 0.010 inches. This preset conformation includes a loop member as described herein, which in some embodiments may be the size of the pulmonary vein antrum of the individual. Referring now to FIG. 4, there is shown a core wire 300 that has been shaped to include a straight portion 302 and a loop member portion 304.

This small diameter core wire 300 is then stretched straight and covered with a small diameter sheath that has sufficient strength/hardness to hold core wire 300 in a substantially straight conformation (i.e., constrain core wire 300) for insertion into the vasculature of an individual. This sheath covered core wire, in a straight conformation, is then inserted into the vasculature of an individual and guided to a desired location, such as the pulmonary vein. Once positioned at the desired location, the small diameter delivery sheath is removed and the core wire assumes its heat set conformation, including the loop member (See FIG. 4), inside of the vasculature of the individual. Once the loop member has formed, an electroporation catheter, including one or more electrodes, is introduced into the vasculature and over the core wire and positioned over the core wire in a desired location for a procedure. In some embodiments, the electroporation catheter that is slid over the core wire to assume the loop member shape may have a durometer value of less than about 50D, or even less than about 40D, or about 35D so that it is sufficiently flexible to slide over the core wire and assume its shape for a procedure.

Once the electroporation catheter including the electrode(s) has been positioned over the core wire, the electroporation procedure can be performed by an operator. Once the procedure is complete, the electroporation catheter may be removed from the core wire by sliding the electroporation catheter over the core wire and removing it. After the electroporation catheter has been removed, a sheath may be introduced over the core wire to put it in a straight conformation as described above so that it can be easily removed from the vasculature of the individual.

Figure 5:
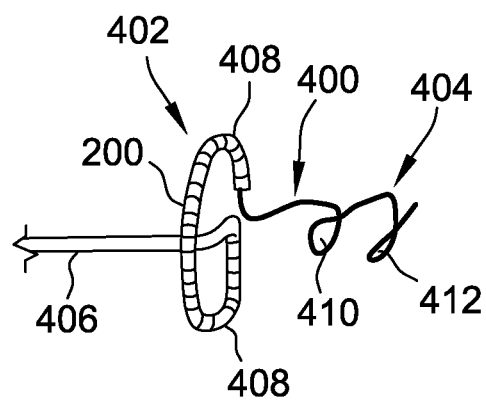
FIG. 5 illustrates the core wire of FIG. 4 further including an anchoring mechanism.

In some embodiments of the present disclosure, the core wire as illustrated in FIG. 4, may additionally include an anchoring mechanism to help anchor the core wire in a desired position within the vasculature during an electroporation procedure. Referring now to FIG. 5, there is shown core wire 400 including loop member 402 and anchoring mechanism 404. FIG. 5 illustrates a catheter 406 positioned over core wire 400 and includes electrodes 408. Anchoring mechanism 404 is sized and configured to anchor core wire 400 in a desired position within the vasculature, such as in the pulmonary vein ostia. The anchoring mechanism may include one or more center loops (illustrated in FIG. 5 as center hoops 410 and 412) to assist in the anchoring of the core wire.

In another embodiment of the present disclosure, a heat sensitive electroporation catheter is disclosed that may be introduced into the vasculature of an individual in a straight conformation and achieve a desired conformation including a loop member on a distal portion thereof as described herein in the vasculature of an individual once in a desired position. In this embodiment the heat-sensitive electroporation catheter includes an outer shaft including one or more electrodes that has a memory shape alloy (such as a nickel-titanium alloy) tube disposed therein. The memory shape alloy tube includes a lumen therein to allow a guidewire to be delivered therethrough. The outer shaft may be constructed of any suitable catheter shaft material, including for example braided and unbraided polyurethanes. The memory shape alloy is preset using a heat treatment or other suitable process to a desired conformation that includes a loop member. This heat treatment (or other suitable process) sets the memory shape alloy to assume a conformation including a loop member at an elevated temperature; that is, the memory shape alloy tube is preset such that it changes conformation from a straight conformation at room temperature to a conformation including a loop member at an elevated temperature, such as the body temperature of an individual. In some embodiments, the conformational change may occur at 30° C., or even 31° C., or even 32° C., or even 33° C., or even 34° C., or even 35° C. or higher. In these embodiments, as the memory shape alloy tube warms inside the body of the individual, it assumes the desired conformation including the loop member. A sheath or similar device may be used as described above to re-straighten the loop member for removal from the body.

Figure 6:
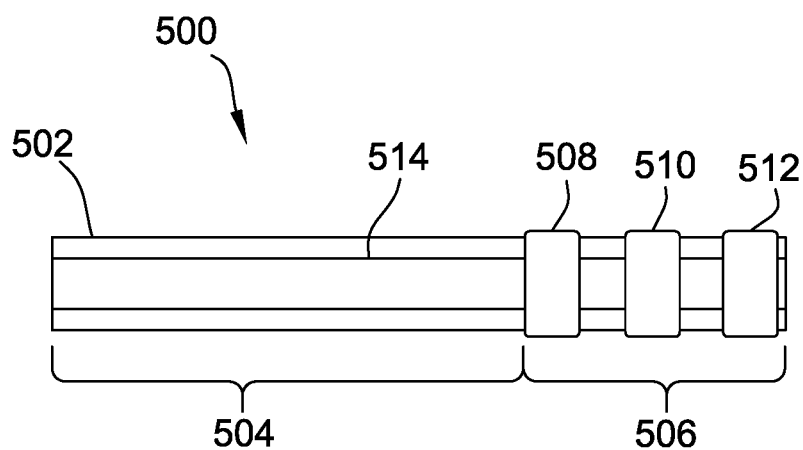
FIG. 6 illustrates a heat-sensitive electroporation catheter capable of forming a loop member in accordance with one embodiment of the present disclosure.

Referring now to FIG. 6, there is illustrated a heat-sensitive electroporation catheter 500 in accordance with one embodiment of the present disclosure. Heat sensitive electroporation catheter 500 includes outer shaft 502 having proximal end portion 504 and distal end portion 506. Distal end portion 506 of heat sensitive electroporation catheter 500 includes electrodes 508, 510, and 512. Heat sensitive electroporation catheter 500 additionally includes memory shape alloy tube 514 disposed within outer shaft 502. Memory shape alloy tube 514 includes a lumen therethrough (not shown in FIG. 6).

As noted above, the present disclosure also relates to methods of introducing an electroporation catheter into the pulmonary vein (or another location) of an individual. In one specific embodiment, a method includes first forming a memory shape wire into a desired preset conformation including a loop member and introducing the formed memory shape wire into a delivery shaft wherein the memory shape wire has a conformation in the delivery shaft different from the preset conformation. Next, the delivery shaft including the memory shape wire is introduced and positioned in the pulmonary vein of the individual and the delivery shaft is removed from the memory shape wire to allow the memory shape wire to achieve its preset conformation including the loop member in the pulmonary vein. Finally, an electroporation catheter including one or more electrodes is introduced over the memory shape wire in the pulmonary vein. Once the electroporation catheter is introduced over the memory shape wire, the electroporation procedure may be completed. This method allows for the formation of the loop member on a distal end portion of the catheter to be formed in the body.

Figure 7:
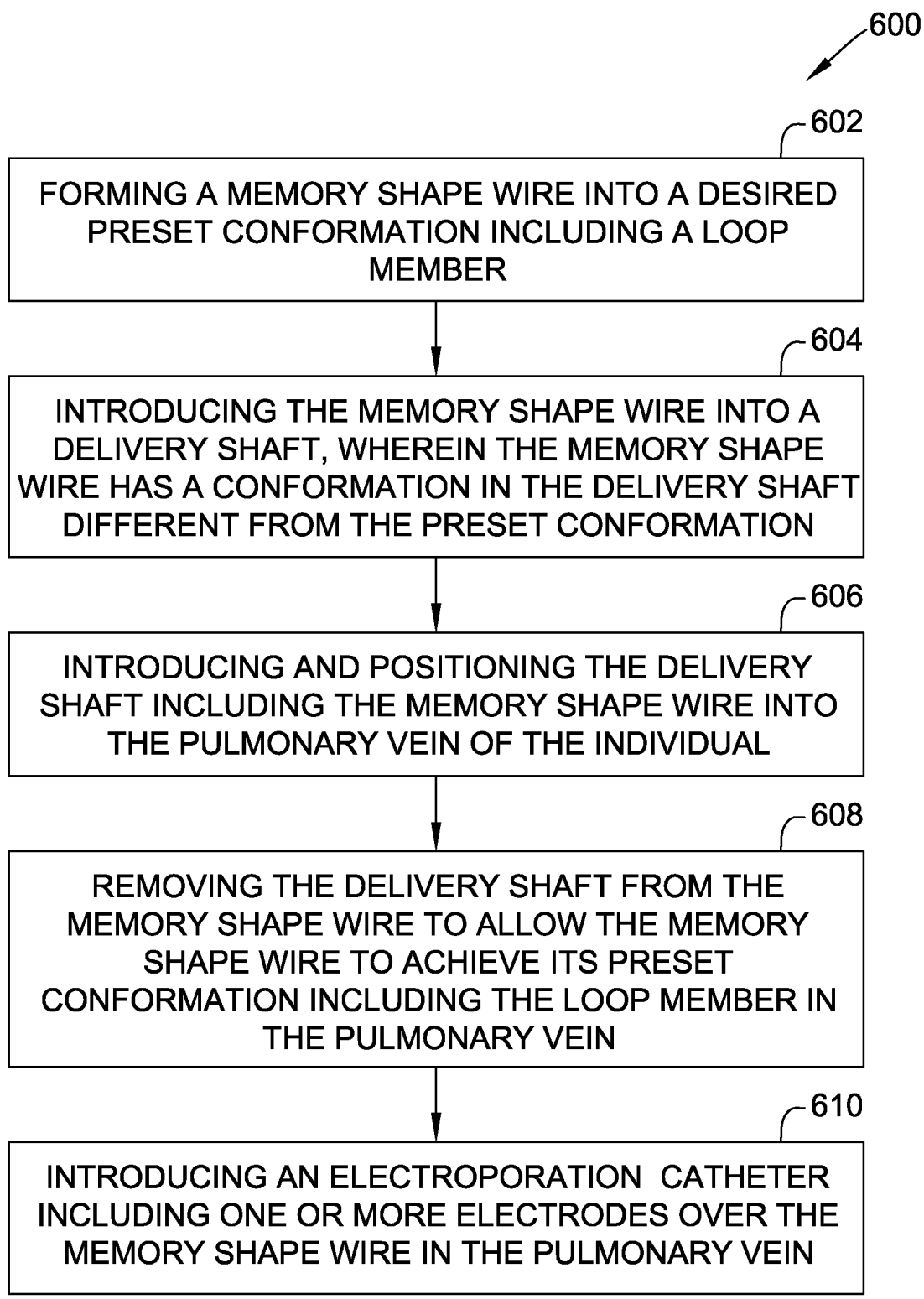
FIGS. 7 and 8 are flow diagrams of methods for introducing an electroporation catheter into a pulmonary vein of an individual.

FIG. 7 is a flow diagram of a method 600 of introducing an electroporation catheter into the pulmonary vein of an individual. Method 600 includes forming 602 a memory shape wire into a desired preset conformation including a loop member and introducing 604 the memory shape wire into a delivery shaft, wherein the memory shape wire has a conformation in the delivery shaft different from the preset conformation. Method 600 further includes introducing and positioning 606 the delivery shaft including the memory shape wire into the pulmonary vein of the individual and removing 608 the delivery shaft from the memory shape wire to allow the memory shape wire to achieve its preset conformation including the loop member in the pulmonary vein. Method 600 further includes introducing 610 an electroporation catheter including one or more electrodes over the memory shape wire in the pulmonary vein. This method allows for the formation of the loop member on a distal end portion of the catheter to be formed in the body.

The present disclosure further relates to another method of introducing an electroporation catheter into a pulmonary view on an individual. In this specific embodiment, the method includes first forming a memory shape braided tube into a preset conformation including a loop member, wherein the preset conformation is achieved at a temperature of about 35° C. or higher, and wherein the memory shape braided tube includes a guidewire lumen therein. Next, the method includes introducing the memory shape braided tube into an outer shaft, wherein the memory shape braided tube has a conformation in the outer shaft different from the preset conformation, and wherein the outer shaft includes one or more electrodes thereon. The outer shaft including the memory shape braided tube is introduced and positioned in the pulmonary vein of the individual over a guidewire and the guidewire is removed. Finally, the memory shape braided tube is allowed to achieve its present conformation such that the memory shape braided tube and the outer shaft including one or more electrodes achieve a conformation including a loop member.

Figure 8:
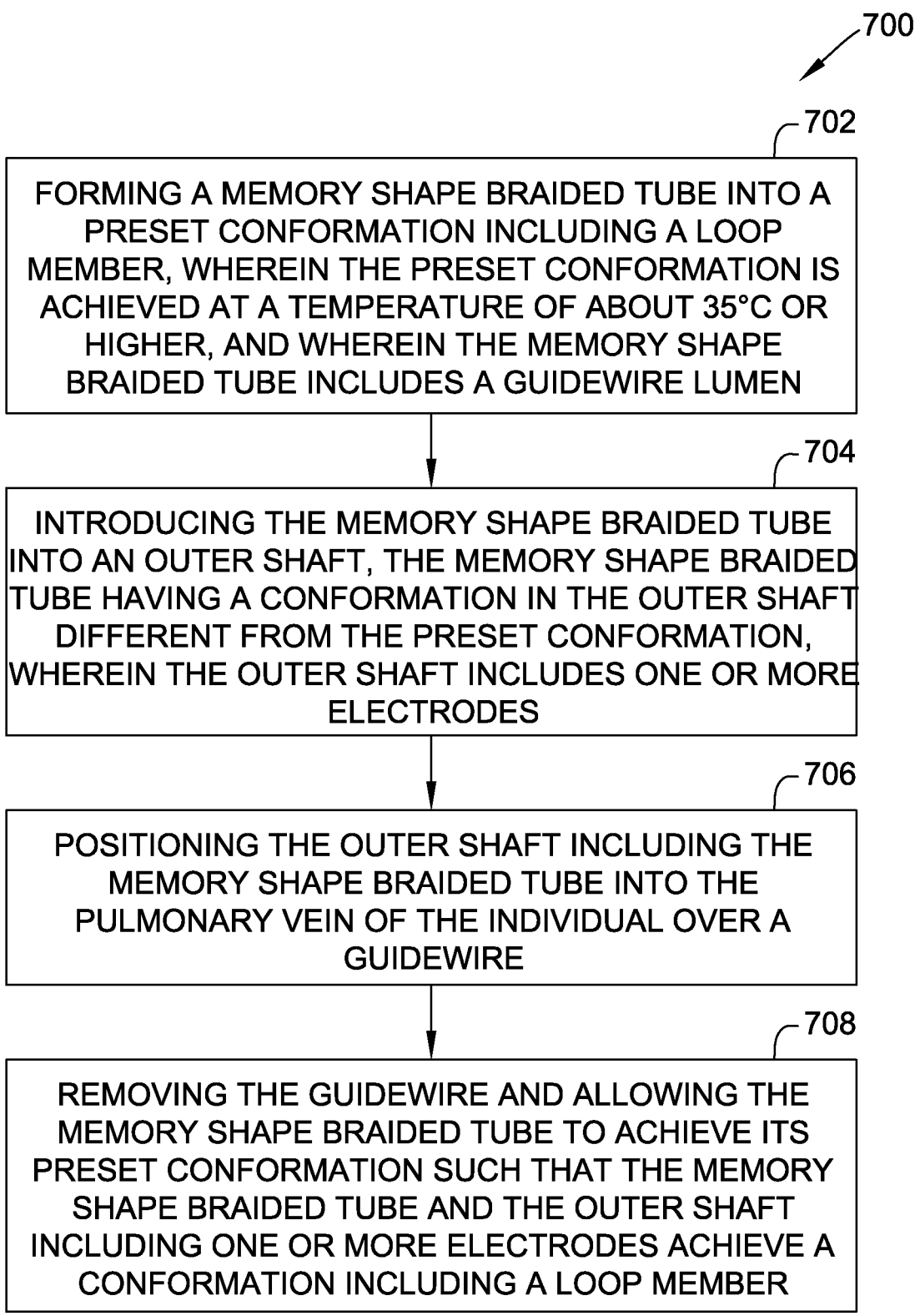

FIG. 8 is a flow diagram of a method 700 of introducing an electroporation catheter into the pulmonary vein of an individual. Method 700 includes forming 702 a memory shape braided tube into a preset conformation including a loop member, wherein the preset conformation is achieved at a temperature of about 35° C. or higher, and wherein the memory shape braided tube includes a guidewire lumen and introducing 704 the memory shape braided tube into an outer shaft, the memory shape braided tube having a conformation in the outer shaft different from the preset conformation, wherein the outer shaft includes one or more electrodes. Method 700 further includes introducing and positioning 706 the outer shaft including the memory shape braided tube into the pulmonary vein of the individual over a guidewire, and removing 708 the guidewire and allowing the memory shape braided tube to achieve its present conformation such that the memory shape braided tube and the outer shaft including one or more electrodes achieve a conformation including a loop member.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An electroporation catheter comprising:
   a longitudinally-extending catheter shaft comprising a proximal end portion and a distal end portion that abuts the proximal end portion at an interface;
   a plurality of electrodes disposed on the distal end portion of the catheter shaft and extending from a proximal electrode to a distal electrode, the proximal electrode positioned proximate the interface;
   a handle attached to the proximal end portion of the catheter shaft; and
   a loop member pull wire in a spiral configuration on an inside surface of the distal end portion of the catheter shaft for forming a loop member on the distal end portion of the catheter shaft, wherein the loop member pull wire is attached to an attachment point in the distal end portion of the catheter shaft and to an attachment point in the handle, wherein the loop member pull wire is in the spiral configuration on the inside surface of the distal end portion while the proximal end portion and distal end portion are in a straight conformation, and wherein, while the proximal end portion and the distal end portion are in the straight conformation, the loop member pull wire transitions from a straight configuration to the spiral configuration proximate the proximal electrode.

2. The electroporation catheter of claim 1, wherein, while the proximal end portion and the distal end portion are in the straight conformation, the spiral configuration of the loop member pull wire completes at least three revolutions on the inside surface of the distal end portion.

3. The electroporation catheter of claim 1, further comprising a guide wire lumen.

4. The electroporation catheter of claim 1, wherein the loop member pull wire is formed from a memory shape alloy.

5. The electroporation catheter of claim 4, wherein the memory shape alloy is a nickel-titanium memory shape alloy.

6. The electroporation catheter of claim 5, wherein the loop member pull wire is heat set to a pre-determined spiral configuration.

7. The electroporation catheter of claim 1, wherein the catheter shaft is formed from a braided material.

8. The electroporation catheter of claim 7, wherein the catheter shaft includes one or more layers of a polyether block amide material.

9. The electroporation catheter of claim 8, wherein the one or more layers of the polyether block amide material includes zones of varying stiffness.

10. The electroporation catheter of claim 9, wherein the distal end portion of the catheter shaft has a different stiffness than the proximal end portion of the catheter shaft.

* * * * *